(12) United States Patent
Levy et al.

(10) Patent No.: US 11,224,330 B2
(45) Date of Patent: Jan. 18, 2022

(54) MEDICAL IMAGING DEVICE WITH CAMERA MAGNIFICATION MANAGEMENT SYSTEM

(71) Applicant: 270 SURGICAL LTD., Netanya (IL)

(72) Inventors: Avraham Levy, Kfar Shmaryahu (IL); Moshe Levi, Ganey Tikva (IL); Victor Levin, Haifa (IL); Golan Salman, Atlit (IL); Amram Aizenfeld, Ramot Menshe (IL); Leonid Krivopisk, Nesher (IL)

(73) Assignee: SURGICAL LTD 270., Netanya (IL)

( * ) Notice: Subject to any disclaimer, the term of this patent is extended or adjusted under 35 U.S.C. 154(b) by 0 days.

(21) Appl. No.: 16/965,304

(22) PCT Filed: Jan. 3, 2019

(86) PCT No.: PCT/IL2019/050014
§ 371 (c)(1),
(2) Date: Jul. 28, 2020

(87) PCT Pub. No.: WO2019/145933
PCT Pub. Date: Aug. 1, 2019

(65) Prior Publication Data
US 2021/0113056 A1 Apr. 22, 2021

Related U.S. Application Data

(60) Provisional application No. 62/622,905, filed on Jan. 28, 2018.

(51) Int. Cl.
*A61B 1/00* (2006.01)
*A61B 1/04* (2006.01)
(Continued)

(52) U.S. Cl.
CPC ........ *A61B 1/0005* (2013.01); *A61B 1/00177* (2013.01); *A61B 1/00188* (2013.01);
(Continued)

(58) Field of Classification Search
CPC ....... A61B 1/00188; A61B 1/042; A61B 1/05; A61B 1/0676; H04N 5/23296; G02B 23/2423; G03B 15/14; G03B 37/04
See application file for complete search history.

(56) References Cited

U.S. PATENT DOCUMENTS 9,848,124 B2 * 12/2017 Iwasaki ................ A61B 1/0005
9,901,244 B2 * 2/2018 Krivopisk ............ A61B 1/0684
(Continued)

*Primary Examiner* — Boubacar Abdou Tchoussou
(74) *Attorney, Agent, or Firm* — Soroker Agmon Nordman

(57) ABSTRACT

A medical imaging device including at least two cameras. The medical imaging device includes an elongated and narrow distal tip connected to a rigid elongated shaft member, wherein the distal tip includes a front camera and a first side camera. The cameras of the disclosed medical imaging device can be configured to provide variable cameras' magnifications, which in some cases may vary from one camera to another. The cameras of the medical imaging device may be provided with dissimilarity in the cameras' magnification factors. Such dissimilarities are used to show the same object in the same size in a panoramic image captured simultaneously by the multiple cameras, as the multiple cameras have multiple distances to the object.

19 Claims, 9 Drawing Sheets

(51) Int. Cl.
  *A61B 1/045* (2006.01)
  *A61B 1/05* (2006.01)
  *H04N 5/232* (2006.01)
  *H04N 5/247* (2006.01)

(52) U.S. Cl.
  CPC .............. *A61B 1/042* (2013.01); *A61B 1/045* (2013.01); *A61B 1/05* (2013.01); *H04N 5/23238* (2013.01); *H04N 5/23296* (2013.01); *H04N 5/247* (2013.01)

(56) References Cited

U.S. PATENT DOCUMENTS

| | | | |
|---|---|---|---|
| 10,009,530 B2* | 6/2018 | Laroia | H04N 5/378 |
| 10,258,222 B2* | 4/2019 | Levin | A61B 1/05 |
| 2005/0270387 A1* | 12/2005 | Watanabe | H04N 5/23203 |
| | | | 348/240.99 |
| 2014/0316198 A1* | 10/2014 | Krivopisk | A61B 1/0011 |
| | | | 600/109 |
| 2015/0293328 A1* | 10/2015 | Laroia | G03B 5/00 |
| | | | 348/369 |
| 2016/0015258 A1* | 1/2016 | Levin | A61B 1/0005 |
| | | | 600/109 |
| 2017/0041537 A1* | 2/2017 | Iwasaki | A61B 1/04 |

* cited by examiner

MEDICAL IMAGING DEVICE WITH CAMERA MAGNIFICATION MANAGEMENT SYSTEM

FIELD OF THE INVENTION

The present invention generally relates to the field of medical instruments designed to capture images from inside the patient's body.

BACKGROUND OF THE INVENTION

A rigid and semi rigid endoscopes are medical imaging devices utilized to perform operations in the abdomen or pelvis through small incisions with the aid of a camera. the endoscope can either be used to inspect and diagnose a condition or to perform surgery. In some cases, procedures which involve inspection of a region inside confined area or a specific body cavity or organ, may also involve the endoscope. Such procedure may include but are not limited to laparoscopes, arthroscopes, cystoscopes, ureteroscopes, hysterectomy and others.

A rigid endoscope is likely to be assembled in an elongated tubular member in which the camera is located in some rigid endoscope devices the electrical circuitry may be found in the control handle of the device, in other rigid endoscope devices the electrical circuitry may be found in the elongated tubular member. In general, the procedure of rigid endoscope starts with a small incision, about 11 millimeters or less, made in the patient body. Thus, the rigid endoscope is required to have a narrow diameter allowing the medical imaging device to be threaded through a relatively small incision at the patient's body. At the same time, in multiple medical procedures, there is a need to obtain a large field of view, and in some cases different view angles on objects captured by the camera.

In some medical procedures, the used rigid endoscope may comprise more than one camera located at the distal end of the rigid endoscope. Thus, the cameras, the optical components and the electrical components may require to be placed in a predefined diameter, typically 10 millimeters or less, adapted to the medical procedure incision made. Apart from the obvious requirement to overcome the challenge of maintaining the required outer diameter when numerous optical gears are placed within the distal tip of the rigid endoscope, the medical imaging devices are required to be designed to provide the wide view possible in order to maintain the performed medical procedures. In some cases, diverse angles of view may be required. In some other cases, a need to provide a wide panoramic view is demonstrated by the users preforming the medical procedures.

SUMMARY OF THE INVENTION

The subject matter disclosed in the present invention discloses a medical imaging device comprising at least two cameras. Said medical imaging device comprises an elongated and narrow distal tip connected to a rigid elongated shaft member, wherein the distal tip can comprise a front camera and a first side camera. Said at least two cameras can be configured to provide variable cameras' magnifications, which in some cases may vary from one camera to another. The distal tip can comprise some optical gear required for the medical procedures, and in some cases, the distal tip may be mounted directly on the rigid shaft. The optical gear located in the distal tip can comprise cameras, lenses and light sources required for the camera functioning.

The distal tip comprises a front camera located on a front planar surface of the distal tip and a first side camera located on a first lateral surface of the distal tip. In some cases, the medical imaging device may also comprise a second side camera located on a second lateral surface of the distal tip. The cameras implemented within the distal tip can be equipped with different lenses characterized with different focal lengths, resulting with dissimilar magnification factors. In such cases, the dissimilarity in the magnification factors of the cameras' lenses can be utilized to achieve a continuous panoramic view formed by the content captured by two or three cameras. The continuous panoramic view is achieved by at least two cameras, wherein the images of an object or objects are displayed at approximately similar sizes in a display of the continuous panoramic view formed inter alia by the cameras' horizontal field of views. In some cases, the fields of views captured by the cameras may be displayed side by side and thereby forming one continuous display. In some other cases, the fields of views of the cameras may be displayed apart from each other and thereby forming at least two displays. For example, the magnification factor of the first side camera may be different than the magnification factor of the front camera in order to receive images of an object at approximately similar sizes the display of the continuous panoramic view formed inter alia by both of the cameras' horizontal field of views.

The magnification of the view captured by the cameras can be the process of enlarging the appearance of an object. Thus, the magnification factor of a particular object captured by a camera is defined herein as the ratio between the appearance size of the object captured by a camera, to the size of the real object. For example, in case a certain object captured by a camera appears on a screen to be twice as large than the real object, the magnification factor can be calculated as two.

In some cases, the dissimilarity in the cameras' magnification factors may also be achieved by a technical manipulation on the video image captured by the cameras with no adjustment of the cameras' optics. For example, the magnification factors of some of the cameras can be achieved by a digital zoom method achieved digitally by computerized based methods configured to enlarge the appearance of the captured objects.

In possible embodiments of the disclosed subject matter, the distance between the lens center of the second side camera and the lens center of the front camera may be smaller than the distance between the lens center of first side camera and the lens center of the front camera. In other possible embodiments of the disclosed subject matter, the distance between the lens center of the second side camera and the lens center of the front camera may be longer than the distance between the lens center of first side camera and the lens center of the front camera. In some cases, a depth of field of the front camera, the second side camera and the first side camera may be in a range of 5 to 150 millimeters. In some cases, the second side camera and the first side camera have a lateral field of view of between 80 to 120 degrees. In some cases, a depth of field of the front camera, the second side camera and the first side camera may be in a range of 1 to 150 millimeters. In some cases, the second side camera and the first side camera have a lateral field of view of between 1 to 120 degrees. In some cases, a depth of field of the front camera, the second side camera and the first side camera may be in a range of 1 to 15 millimeters. In some cases, the second side camera and the first side camera have a lateral field of view of between 1 to 12 degrees.

In some cases, the distal tip may further comprise at least one aperture shaped for securing the first side camera, the front camera and the second side camera. In some cases, said apertures may have opaque walls with transparent apertures located near the front camera, the first side camera, and the second side camera. The distal tip may further comprise a front illumination module for illuminating the area captured by the front camera, a lateral illumination module for illuminating the area captured by the second side camera, and a lateral illumination module for illuminating the area captured by the first side camera. Thus, the front illumination module may comprise two illumination units on both sides of the front camera, wherein one illumination unit may be bigger than the other in case the front camera may not be positioned in the center of the front surface.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

The present specification discloses a medical imaging device which can be utilized when obtaining a panoramic view, wherein the medical imaging device is required to pass through an incision in the body to facilitate medical procedures at the body's internal organs. Such a medical imaging device can comprise two or three cameras designed to aid medical procedures such as inspection or surgery.

As used in the specification, the term "optical gear" is used to depict a set of components that allows the medical imaging device to capture light and transform that light into at least one image. In some embodiments, lenses are employed to capture light and image capturing devices, such as sensors, are employed to transform that light into at least one image. In some embodiments, a camera comprises a plurality of optics such as lens assembly and sensor, and is configured to receive reflected light from target objects.

Image capturing devices may be Charged Coupled Devices (CCD's) or Complementary Metal Oxide Semiconductor (CMOS) image sensors, or other suitable devices having a light sensitive surface usable for capturing an image. In some embodiments, a sensor such as a Charge Coupled Device (CCD) or a Complementary Metal Oxide Semiconductor (CMOS) image sensor (for detecting the reflected light received by an optical element), is employed.

In some embodiments of the disclosed subject matter, the cameras of the medical imaging device may be provided with dissimilarity in the cameras' magnification factors. Such dissimilarities are used to show the same object in the same size in a panoramic image captured simultaneously by multiple cameras, as the multiple cameras have multiple distances to the object. In some cases, the dissimilarity in the cameras' magnification factors may be achieved by cameras with lenses, or in some cases, lens assemblies characterized by different focal lengths. In some cases, the dissimilarity in the cameras' magnification factors may be achieved by cameras with sensors characterized by different sizes. In some cases, the cameras in the medical imaging device may be configured such that the required ratio between the magnification factors may be achieved for objects and located within the defined depth of field of the cameras.

In some embodiments of the disclosed subject matter, dissimilarity in the cameras' magnification factors may be achieved by a contribution of electronic process configured to adjust the cameras' magnification factors, such that the required ratio between the magnification factors may be achieved for objects located within the defined depth of field of the cameras.

Figure 1A:
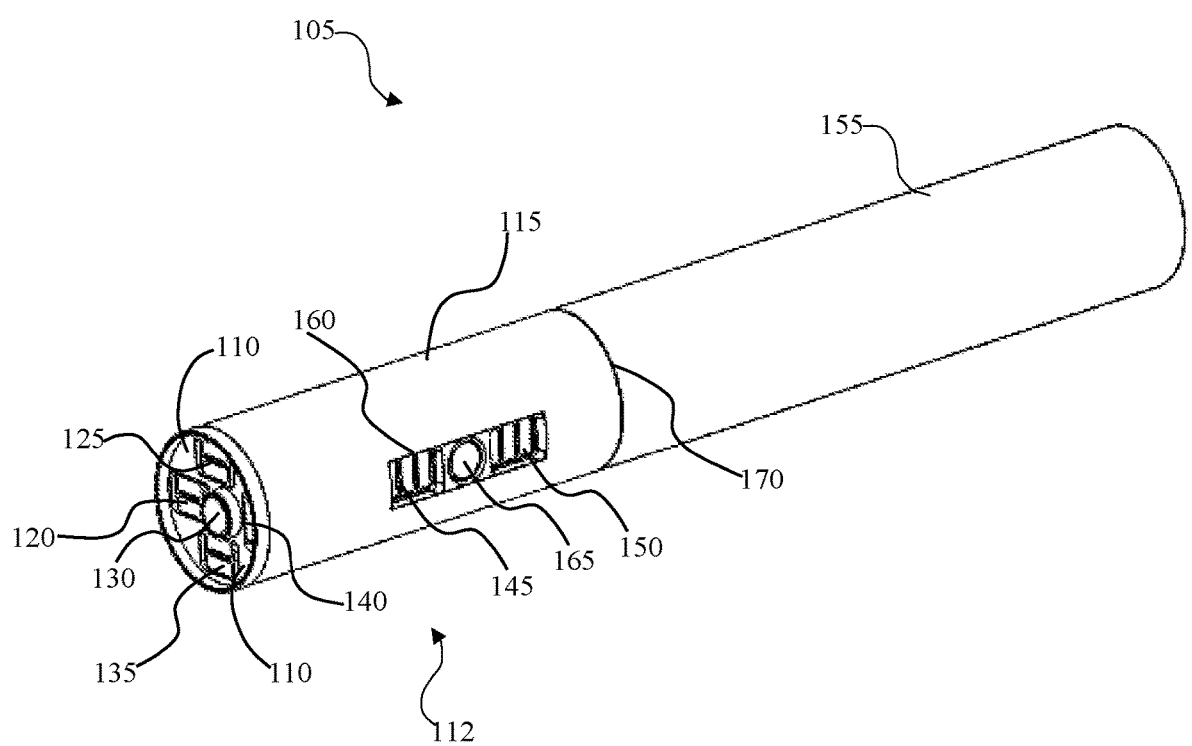
FIG. 1A demonstrates a medical imaging device comprising at least two cameras, according to exemplary embodiments of the disclosed subject matter.

FIG. 1A demonstrates a medical imaging device comprising at least two cameras, according to exemplary embodiments of the disclosed subject matter. FIG. 1 shows a medical imaging device 105 comprising a rigid elongated shaft 155 designed to be directly connected to a distal tip component 115, wherein the distal tip component 115 may cover and seal the optical gear (not shown) of the distal tip 112. In such cases, a seamline 170 outlines the connection line between the elongated rigid shaft 155 and the distal tip component 115. In some cases, the elongated rigid shaft 155 and the distal tip component 115 may be connected by an adhesive material that seals the connection at the seamline 170. In some other cases, the elongated rigid shaft 155 and the distal tip component 115 may be connected by soldering. In possible embodiments of the disclosed subject matter, the elongated rigid shaft 155 and the distal tip component 115 may be connected by a screwing mechanism which fastens the elongated rigid shaft 155 and the distal tip component 115 together. In yet another embodiment (not shown), the elongated rigid shaft 155 extends along the length of medical imaging device 105 and covers the distal tip 112.

The distal tip 112 may function as a multi-camera section member designed to house at least two cameras. In some cases, one or more cameras of the distal tip 112 may be located in the front section of the distal tip 112, at a front planar surface 110. Additional cameras may be located at the lateral round surface of the distal tip component 115. The lateral round surface of the distal tip component 115 may also comprise an aperture 160 shaped to house a second side camera 165 and provides the opening required for the field of view of the second side camera 165. In some cases, the aperture 160 may be covered by a transparent layer, such as glass or plastic, to isolate the second side camera 165 from the patient's tissue. In some other cases, aperture 160 may be covered by an optical window or more than one optical window.

In some embodiments, the distal tip 112 may comprise a first side camera (not shown) located at the opposite side of the distal tip 112. The aperture 160 also enables emission of light from side illuminators 150, and 145 which provide the light source to the direction of the area captured by the second side camera 165. In some cases, the light may be emitted by dedicated section illuminators such as light-emitting diodes, also known as LED.

The distal tip 112 may also comprise a front camera 130. The front camera 130 may be situated at the center of front planar surface 110 housing the front camera 130 and providing the opening required for the field of view of the front camera 130. The planar surface 110 also comprise front illuminators 120, 125, 135, and 140 which provide the required source of light for the front camera 130. In other possible embodiments, the number and location of front illuminators may vary, for example, less than 4 set of illuminators or more wherein each set of illuminators has 1, 2, 3, 4 or more LED and may emit the same light spectrum.

In some embodiments of the disclosed subject matter, the cameras located within the distal tip component 115 may have different magnification factors and thereby scale up the view captured by the lens in different sizes. For example, in case the magnification factor of the second side camera 165 is twice as large than the magnification factor of the front camera 130. In such case, an object located at a distance to the front camera 130 which is shorter compared to the distance to the second side camera 165 may be captured by at approximately similar sizes and thereby allows a forming of a continuous panoramic view by said two cameras.

In some cases, the magnification factor may depend on the focal length of the camera. For example, the second side camera 165 may be provided with a lens or a lens assembly with a focal length which is twice larger than the focal length of the lens of the front camera 130. In some cases, the focal length of the second side camera 165 and the front camera 130 may also be different, in order to achieve different magnification factors of the cameras.

In some cases, the magnification factor may depend on the size of the camera's sensor. For example, second side camera 165 may be provided with a sensor with a size which is twice larger than the size of the sensor of front camera 130.

Figure 1B:
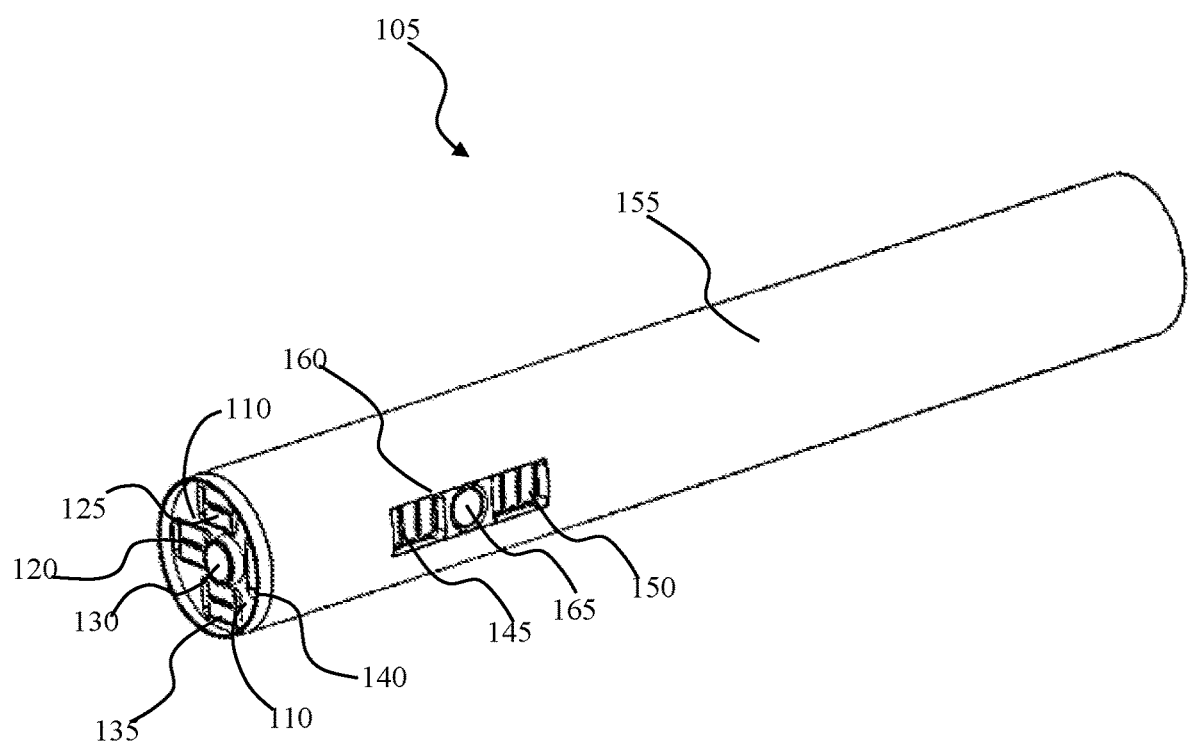
FIG. 1B demonstrates a medical imaging device comprising a rigid shaft which comprises an optical gear required for the operation of the medical imaging device, according to FIG. 1A.

FIG. 1B demonstrates a medical imaging device comprising a rigid shaft which comprises an optical gear required for the operation of the medical imaging device, according to FIG. 1A. FIG. 1B shows a medical imaging device 105 comprising one rigid shaft 155 without a distal tip. The rigid shaft 105 may function as a multi-camera section member designed to house at least one camera. In some cases, the cameras may be positioned at the edge of the rigid shaft 155 located in the front at the planar surface 110. In some other cases, the cameras may be located at the cylindrical round surface of the rigid shaft 155 at a distance between 6.5 to 40 millimeters from front panel 110. In yet another embodiment, a front camera may be positioned at the edge of the rigid scope at front panel 110 and one or more side cameras may be located at the cylindrical round surface of the rigid shaft 155 at a distance between 6.5 to 40 millimeters from front panel 110.

The rigid shaft 155 may also comprise an aperture 160 shaped to house a second side camera 165 and provide the field of view operatively required for the second side camera 165. In some embodiments of the disclosed subject matter, the rigid shaft 155 may comprise a first side camera (not shown) located at the opposite side of the rigid shaft 155 within a first side aperture (not shown). The aperture 160 also houses side illumination modules 150 and 145 which provide the light source of the side camera 165. In some cases, the light source may be emitted by dedicated illuminators such as light-emitting diode, also known as LED. In some cases, each illumination module has 1, 2, 3, 4 or more LED and emit different light spectrum as will explained above.

The rigid shaft 155 may also comprise a front camera 130 which may be situated closer to one of at the center of a front planar surface 110 which can house the front camera 130 and provide the field of view operatively required for front camera 130. The front planar surface 110 may also comprise front illuminators' sets 120, 125, 135, and 140 which provide the required source of light for front camera 130. In some cases, each illumination module has 1, 2, 3, 4 or more LED and may emit the same light spectrum or different light spectrum as was explained above. In another embodiment, front camera 130 may be situated at the center of the front planar surface 110.

In some cases, the rigid shaft 155 may be prepared as a one-piece. For example, rigid shaft 155 may be prepared by a molding process. In some cases, the preparation process of the rigid shaft 155 may also comprise a milling process for creating the apertures for the cameras, the rounded surfaces, the planar surfaces, the room for the cameras, and the like.

In some embodiments of the disclosed subject matter, the cameras located within the rigid shaft 155 may have different magnification factors. For example, the second side camera 165 may be provided in a magnification factor which is two times larger than the magnification factor of the front camera 130 magnification factor. In some cases, focal length of the second side camera 165 and the front camera 130 may also be different, in order to achieve the differences in the magnification factors of the cameras. In some cases, sensor size of the second side camera 165 and the front camera 130 may also be different, in order to achieve the differences in the magnification factors of the cameras. In some cases, the medical imaging device 105 may be connected to a main control unit (not shown) which can receive the video images of the front camera 130 and the second side camera 165, as explained above.

In some cases, the magnification factor may depend on the size of the camera's sensor. For example, second side camera 165 may be provided with a sensor with a size which is twice larger as the size of the sensor of front camera 130.

Figure 2A:
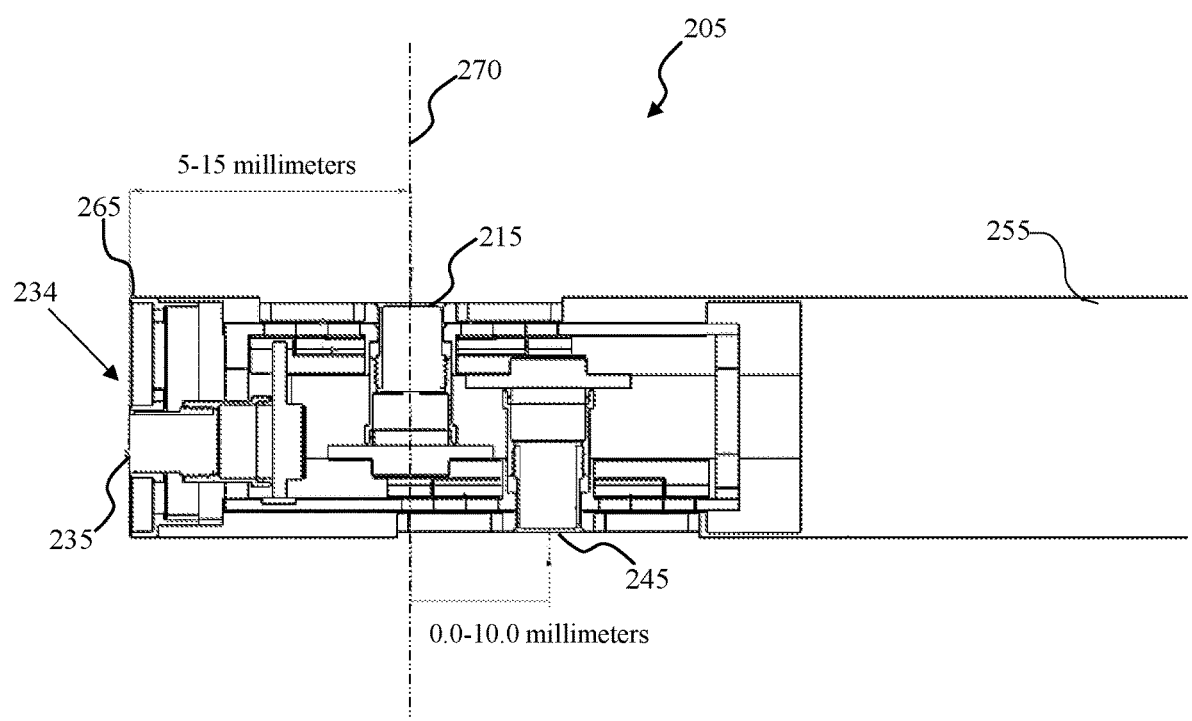
FIG. 2A demonstrates an upper cross section of a distal tip comprises one front camera and two side cameras, according to exemplary embodiments of the disclosed subject matter.

FIG. 2A demonstrates an upper cross-section of a distal tip comprises one front camera and two side cameras, according to exemplary embodiments of the disclosed subject matter. FIG. 2A shows the distal tip 205 designed to be connected to a rigid shaft such as rigid shaft 255 by an adhesive or by soldering, or in some cases by a screwing mechanism which fastens the rigid shaft 255 and distal tip 205 together. In another embodiment, distal tip 205 may be the distal end of rigid shaft 255, such rigid shaft 255 and distal tip 205 may be one component as disclosed above.

The distal tip 205 shown in the exemplary case demonstrated in FIG. 2A can comprise three cameras, a first side camera 215, a second side camera 245 and a front camera 235. The front camera 235 is situated at the front planar surface 234 located at the tip edge point 265 of the distal tip 205. In some cases, the front camera 235 may be situated closer to one of the sides of the front planar surface 234. In FIG. 2A, the front camera 235 can be located closer to the side of the second side camera 245. With regard to the first side camera 215, said camera can be situated such that the center of the first side camera 215 can be located approximately 5.0 to 15.0 millimeters from tip edge point 265. With regard to the distal tip 205, said camera can be situated such that the center of the second side camera 245 can be located approximately 0.0 to 10.0 millimeters from a vertical axis 270 which crosses the center of the first side camera 215.

In some cases, when the centers of the two side cameras, 215 and 245, are not located on the same vertical axis (i.e., aligned with vertical axis 270), as shown in the exemplary case of FIG. 2A, the focal lengths of the lenses of each of the side cameras may be different. In such cases, the focal length of the lenses of the front camera 235 may also be different from the focal length of the lenses of the first side camera 215 and the second side camera 245, in order to provide different magnification factors, and thereby provide a continuous panoramic view formed by the three cameras. In some cases, the dissimilarity of the lenses' focal lengths of the cameras may be utilized to achieve the dissimilarity of the magnification factors of the cameras, thus compensating on the difference in distances between each camera and the field of view, or a specific object therein. For example, the focal length of the front camera 235 lenses may be shorter than the focal length of the first side camera 215 lenses which may result in different magnification factors of the both cameras, wherein in some cases, longer focal length of the lens causes a larger camera's magnification factor.

In some cases, the focal length of the first side camera 215 lenses may be longer than the focal length of the second side camera 245 lenses. In such case, the magnification factor of the second side camera 245 lenses can be smaller than the magnification factor of the first side camera 215.

In some cases, the magnification factor may change within the field of view of a camera, according to a formula based on $M=f/f-D$ wherein M is the magnification factor, f is the focal length and D is the distance to the lens.

Figure 2B:
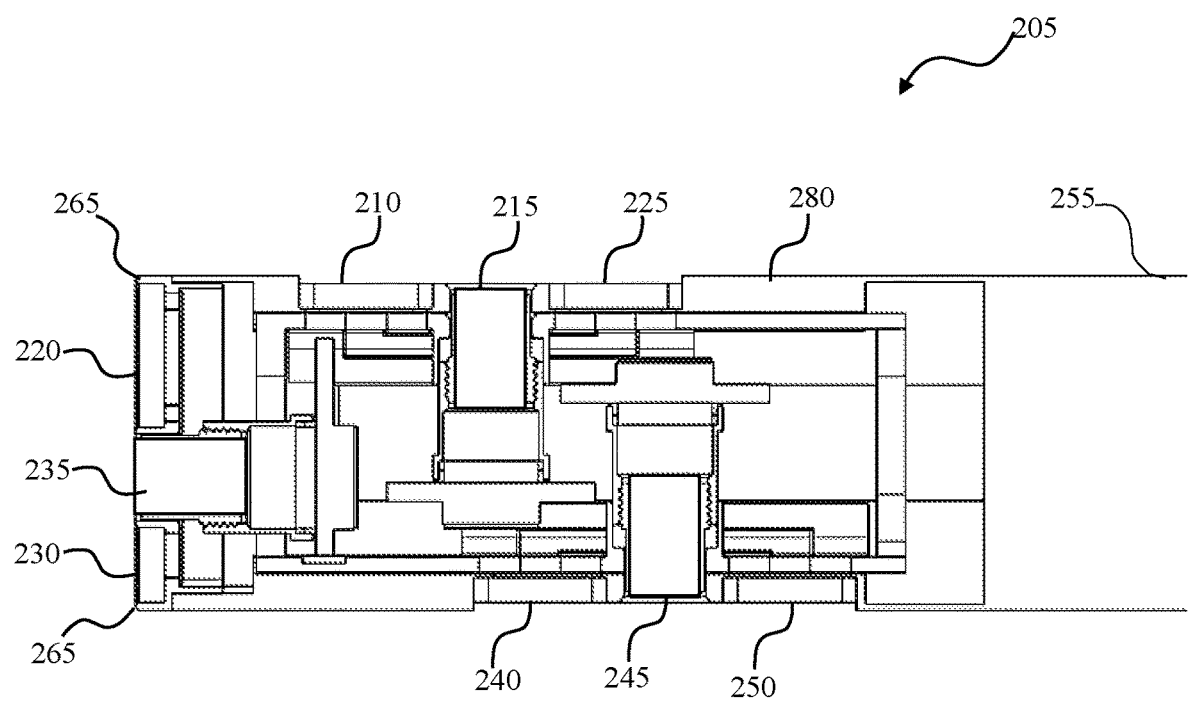
FIG. 2B demonstrates an upper cross section of a medical imaging device that comprises three cameras, according to exemplary embodiments of the disclosed subject matter.

FIG. 2B demonstrates an upper cross section of a medical imaging device that comprises three cameras, according to exemplary embodiments of the disclosed subject matter. FIG. 2B shows a medical imaging device 205 with a rigid shaft 255 and a distal tip 280 comprising three cameras such as a front camera 235, first side camera 215, and second side camera 245. The distal tip 280 also comprises a tip edge point 265 housing the front camera 235 wherein the front camera 235 comprises a front lens assembly and a front sensor for capturing a predefined front field of view. In some exemplary cases, the field of view of the front camera 235 may be at least 100 degrees with a depth of field of approximately 15 to 150 millimeters. The first side camera 215 comprises a first side lens assembly and a first side sensor for capturing a predefined first side field of view. In some exemplary cases, the field of view of the first side camera 215 may be at least 100 degrees with a depth of field of approximately 15 to 150 millimeters. Second side camera 245 comprises a second side lens assembly and a second side sensor for capturing a predefined second side field of view.

In some exemplary cases, the field of view of the second side camera 245 may be at least 100 degrees with a depth of field of approximately 15 to 150 millimeters.

In such exemplary cases, different magnification factors may by applied for the three cameras in order to provide a continuous panoramic view formed by the three cameras. In some cases, the medical imaging device 205 may be configured and adapted such that, the continuous panoramic view may be displayed in a display device (not shown). A magnification factor of the first side camera 215 and second side camera 245 may be twice larger than the magnification factor of the front camera 235 for a given depth of field. For example, in case the front camera 235 comprises a lens assembly provided with a focal length of about 1.7 millimeters and first side camera 215 and the second side camera 245 comprise a lens assembly provided with a focal length of 3.4 millimeters, and wherein first side camera 215 and second side camera 245 may be provided each with a sensor with a size which is twice larger as the size of the sensor of front camera 235, the magnification factor of the side cameras 215 and 245 may be essentially twice larger than the magnification factor of the front camera 235, for objects which are located at a distance of about 15 to 150 millimeters from the lenses of both of said front and side cameras.

In some embodiments of the disclosed subject matter, differences in the magnification factors of the cameras, first side camera 215, second side camera 245, and front camera 235 may be also achieved by a technical/image manipulation on the video image captured by the cameras, as aforementioned. For example, the front camera 235, the first side camera 215 and second side camera 245 may comprise lens assemblies provided with the same focal length and the same sensor size which may result in the same magnification factor for three cameras. In such cases, a technical procedure such as digital zoom may be utilized to manipulate the video image captured by the cameras to achieve different magnification factors thus provide a continuous panoramic view which in some cases, may be displayed in a display device (not shown). In some cases, the first side camera 215 and the second side camera 245 may be situated back to back, namely the distance between center of the first side camera 215 and the center of the front camera 235 is essentially equal to the distance between the center of the second side camera 245 and the center of the front camera 235. In such cases, the magnification factors of the first side camera 215 and the second side camera 245 may be essentially equal.

The medical imaging device 205 may also comprise front illumination modules 220 and 230, first side illumination modules 210 and 225, and second side illumination modules 240 and 250. The illumination module may be LEDs emitting light required for the operation of the associate cameras. For example, front illumination module 220 and 230 adapted to emit light aligned with front camera 235 field of view, first side illumination module 210 and 225 adapted to emit light aligned with first side camera 215 field of view, and second side illumination module 240 and 250 adapted to emit light aligned with second side camera 245 field of view. In some cases, the number of illumination modules of each camera may be more than one. In some cases, each illumination module may include 1, 2, 3, 4 or more LEDs and emit the same light spectrum or different light spectrum. The illumination modules 220, 230, 225, 210, 240 and 250 may receive electrical power via a cable placed in the rigid shaft 255. In some embodiments of the disclosed subject matter, the light emitted by the LEDs may be a white light. In some other cases, a portion of the light sources of the medical imaging device 205 may be at different colors at the visible light. For example, the light source of the medical imaging device 205 may comprise LEDs emitting other colors such as blue, red, yellow, green, or any combination thereof. In some cases, the light emitted by the LEDs may be at the spectrum of the non-visible light. For example, a light source can provide a light at the infrared spectrum, ultra-violate, x-ray, and the like.

Figure 3A:
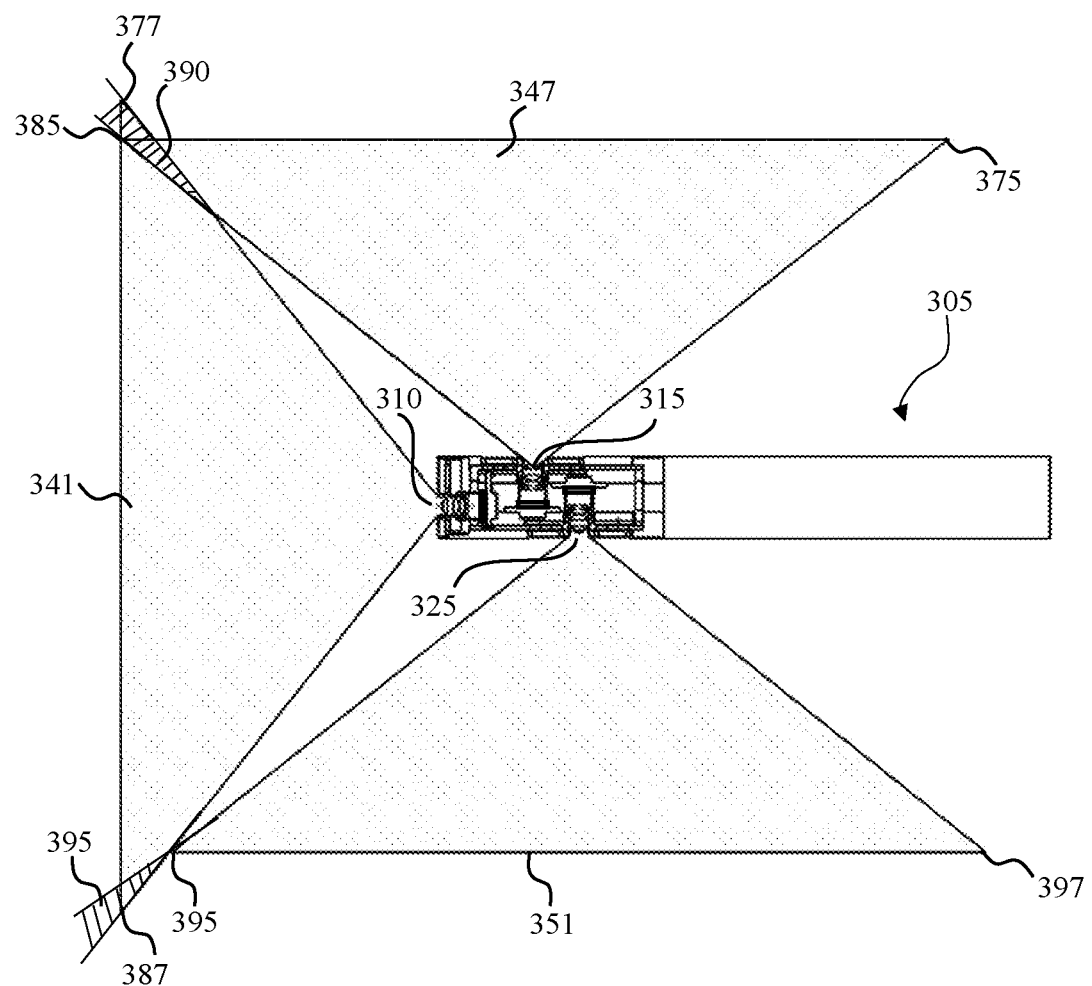
FIG. 3A demonstrates three fields of view of three cameras in a medical imaging device, according to exemplary embodiments of the disclosed subject matter.

FIG. 3A demonstrates three fields of view of three cameras in a medical imaging device, according to exemplary embodiments of the disclosed subject matter. FIG. 3A shows a medical imaging device 305 comprising three cameras, a front camera 310, a second side camera 325 and a first side camera 315. The front camera 310 may be provided with a horizontal Field of View (FOV) 341. The horizontal FOV 341 can be defined as the imaginary triangle representing the observable view of the front camera 310, for example defined by the front camera 310, point 377, and point 387. Point 385 outlines one of the edges of a horizontal field of view of first side camera 315, denoted as horizontal FOV 347. The horizontal FOV 347 can be the imaginary triangle representing the observable view of the first side camera 315 and defined by the first side camera 315, point 385 and point 375. In some cases, some of the seen areas of horizontal FOV 341 may be also seen in horizontal FOV 347. Thus, a first overlap FOV area 390 refers to areas seen simultaneously at both horizontal FOVs, 341 and 347. In some embodiments, horizontal FOV 341 is equal to horizontal FOV 347 and has a value in a range of 100 to 160 degrees.

In some cases, the first side camera 315 may have a different magnification factor relative to the front camera 310 in order to achieve a continuous panoramic view formed by the cameras which can be displayed in a display device (not shown). For example, the magnification factor of the first side camera 315 may be different than the magnification factor of the front camera 310 in order to receive images of an object at approximately similar sizes in both of the cameras' horizontal field of views, in such cases wherein the distance between the object to each of the cameras is different, yet the distance between the object to front camera 310 and the distance between the object to first side camera 315 is larger than 11 millimeters. In such an exemplary case, said object can be seen at the overlap FOV area 390, wherein the distance of the object to the front camera 310 is shorter than the distance of the object to the first side camera 315. The dissimilarity of the magnification factors of both said cameras 310, 315 may allow to receive inspected objects at approximately similar sizes and thereby create one continuous view formed from the images captured by the two said cameras. For example, the first side camera 315 may be provided in a magnification factor which is one and a half (1.5) times larger than the magnification factor of the front camera 310. In that exemplary case, an object located closer to the front camera 310 than the distance to the first side camera 310 can be sensed at the same size from both cameras. In some cases, the focal length of the first side camera 315 and the front camera 310 may be dissimilar, in order to achieve the dissimilarity in the magnification factors of the cameras. In some cases, the sensor size of the first side camera 315 and the front camera 310 may be dissimilar, in order to achieve the dissimilarity in the magnification factors of the cameras. For example, the front camera 310 may be provided with a focal length of 1.58 millimeters and comprise an image sensor at the size of ⅙ inch, and the first side camera 315 may be provided with a focal length of 3.16 millimeters and comprise an image sensor at the size of ⅓ inch. In such cases, the magnification factor of the first side camera 315 may be one (1) and the magnification factor of the front camera 310 may be two (2).

Point 397 outlines one of the edges at the horizontal field of view of the second side camera 325, denoted as horizontal FOV 351. The horizontal FOV 351 can be defined as the imaginary triangle defining the observable view seen from the second side camera 325 and defined with the second side camera 325, the point 397 and the point 395. In some cases, some of the seen areas of horizontal FOV 341 may also be seen in horizontal FOV 351. Thus, a second overlap FOV area 395 refers to areas seen simultaneously at both horizontal FOVs, 341 and 351. In some embodiments, horizontal FOV 341 is equal to horizontal FOV 351 and has a value in a range of 100 to 160 degrees.

In some cases, the second side camera 325 may also be provided with a different magnification factor relative to the front camera 310 in order to receive images of an object at approximately similar sizes in both of the cameras' horizontal field of views, in case said object is seen at the overlap FOV area 395, wherein the object is closer to the front camera 310 than to the second side camera 325, yet the distance between the object to front camera 310 and the distance between the object to second side camera 325 is larger than 11 millimeters. For example, the second side camera 325 may be provided with a magnification factor which is two times larger than the magnification factor of the front camera 310. In some cases, the focal length of the second side camera 325 and the front camera 310 may also be different, in order to achieve the dissimilarity in the magnification factors of the cameras.

In possible embodiments, when the location of each of side cameras 315 and 325, relative to the front camera 310 is different, the size of the first overlap FOV 390 and the size of the second overlap FOV 395 may not be equal. Said configuration and an unequal magnification factor of the front camera 310, first side camera 315 and second side camera 325 may allow to achieve a continuous panoramic view formed by the views captured by the cameras. For example, in some cases, during a medical procedure when the medical imaging device 305 is utilized to inspect a certain area within a body, some of the inspected area may be in both FOV 351 and FOV 341, at the second overlap FOV area 395. In such cases, the different magnification factor of front camera 310 and second side camera 325 may allow to achieve a continuous panoramic view formed by the views captured by the cameras.

In some cases, the overall FOV created by the front camera 310, first side camera 315 and second side camera 325 may reach approximately 250 degrees, without any object seen in two different views. In some cases, the overall FOV created by the front camera 310, first side camera 315 and second side camera 325 may reach approximately 270 degrees, without any object seen in two different views. For example, in case an object located within the overlap FOV area 390 is seen by both of the cameras, first side camera 315 and front 310, a continuous panoramic view formed by the cameras with said object at one size may be achieved.

In some cases, the second side camera 325 may also have a dissimilar magnification factor relative to the first side camera 315 in order to achieve a continuous panoramic view formed by the first side camera 315, the second side camera 325, and the front side camera 310.

Figure 3B:
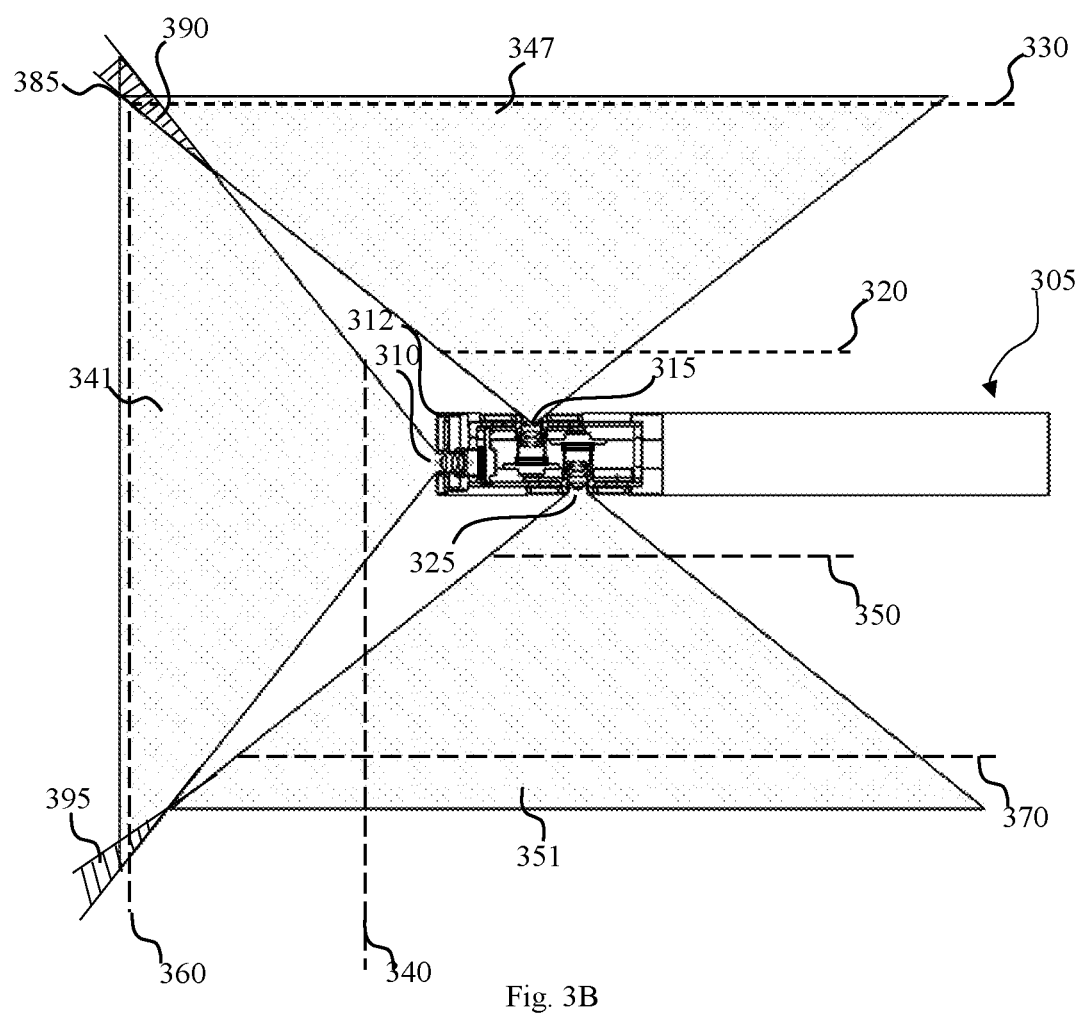
FIG. 3B demonstrates a depth of field in three fields of view of the three cameras in a medical imaging device, according to FIG. 3A.

FIG. 3B demonstrates a depth of field in three horizontal fields of view of the three cameras in a medical imaging device, according to FIG. 3A. FIG. 3B shows a medical imaging device 305 comprising three cameras, the front camera 310, the second side camera 325 and the first side camera 315. The front camera 310 can be provided with horizontal Field of View (FOV) 341, the first side camera 315 can be provided with horizontal Field of View (FOV), denoted as FOV 347. The second side camera 325 can be provided with horizontal Field of View (FOV), denoted as FOV 351. The front camera 310 may be characterized with a front depth of field (DOF) defined by the imaginary field located between the dotted lines 340 and 360 placed horizontally to front planar surface 312. In some cases, the dotted lines 340 may be between 5 to 25-millimeter distance from the front side camera 310 and the dotted line 360 may be between 80 to 200-millimeter distance from the front side camera 310. In some cases, the dotted lines 340 may between 10 to 15-millimeter distance from the front side camera 310 and the dotted line 360 may be between 120 to 150-millimeter distance from the front side camera 310. In some cases, the dotted lines 340 may between 15 to 35-millimeter distance from the front side camera 310 and the dotted line 360 may be between 150 to 200-millimeter distance from the front side camera 310. In such cases, the effective focus of the front side camera 310 may be at the imaginary area between the dotted line 340 and the dotted line 360.

In some cases, the first side camera 315 may be characterized with a first side depth of field (DOF) defined by the imaginary area located between the dotted lines 320 and 330 placed horizontally to first side camera surface 315. The dotted lines 320 may be between 5 to 80-millimeter distance from the first side camera 315 and the dotted line 330 may be between 100 to 250-millimeter distance from the first side camera 315. In some embodiments, dotted lines 320 may be between 20 to 60-millimeter distance from the first side camera 315 and the dotted line 330 may be between 150 to 200-millimeter distance from the first side camera 315. In some embodiments, the dotted lines 320 may be between 50 to 80-millimeter distance from the first side camera 315 and the dotted line 330 may be between 180 to 250-millimeter distance from the first side camera 315. In such cases, the effective focus of the first side camera 315 may be at the imaginary field between the dotted line 320 and the dotted line 330.

The second side camera 325 may also be characterized with a second side depth of field (DOF) defined by the imaginary field located between the dotted lines 350 and 370 placed horizontally to second side camera surface 325. In some cases, the dotted lines 350 may be between 5 to 80-millimeters distance from the front second side camera 325 and the dotted line 370 may be between 100 to 250 millimeters distance from the front second side camera 325. In some embodiments, dotted lines 350 may be between 20 to 60-millimeter distance from the second side camera 325 and the dotted line 370 may be between 150 to 200-millimeter distance from the second side camera 325. In some embodiments, dotted lines 350 may be between 50 to 80-millimeter distance from the second side camera 325 and the dotted line 370 may be between 180 to 250-millimeter distance from the second side camera 325. In such cases, the effective focus of the second side camera 325 may be at the imaginary field between the dotted line 350 and the dotted line 370.

In some cases, the first side camera 315 may have a different magnification factor relative to the front camera 310 in order to achieve a continuous panoramic view formed by the first side camera 315 and the front camera 310. In some embodiments of the disclosed subject matter, the continuous panoramic view formed by the first side camera 315 and the front camera 310 may take place within the imaginary area defined by the DOF of the first side camera 315 and the front camera 310. For example, the first side camera 315 and the front camera 310 may be configured such that the dissimilarity of the magnification factors can be utilized to create a continuous panoramic view for objects and areas located within the overlap FOV area 390 and within the DOF of the first side camera 315 defined between the dotted lines 320 and 330, and the DOF the front camera 310 defined between the dotted lines 340 and 360.

For example, in case an object is seen at the overlap FOV area 390, wherein the distance of the object to the front camera 310 is smaller than the distance of the object to the first side camera 315, the magnification factor of the first side camera 315 may be different in order to receive said object at similar sizes in both of the cameras' field of views, wherein the object is located within the DOF of the first side camera 315 defined between the dotted lines 320 and 330, and the DOF the front camera 310 defined between the dotted lines 340 and 360.

In some cases, the second side camera 325 may also have a different magnification factor relative to the front camera 310 in order to achieve a continuous panoramic view using the views captured by the cameras. For example, in case an object is seen at the overlap FOV area 395, wherein the distance of the object to the front camera 310 is shorter than the distance of the object to the second side camera 325, the magnification factor of the second side camera 325 may be different the front camera 310, in order to receive said object at approximately similar sizes in both of the cameras' field of views. The object may be required to be located within the DOF of the second side camera 325 defined between the dotted lines 350 and 370, and the DOF the front camera 310 defined between the dotted lines 340 and 360. In some cases, the second side camera 325 may be provided in a magnification factor which is two times larger than the magnification factor of the front camera 310, for objects located within the DOF of the second side camera 325 defined between the dotted lines 350 and 370.

In some cases, the overall FOV created by the front camera 310, first side camera 315 and second side camera 325 may reach approximately 250 degrees, without any object seen in two different views. In some cases, the overall FOV created by the front camera 310, first side camera 315 and second side camera 325 may reach approximately 270 degrees, without any object seen in two different views. For example, in case an object located within the overlap FOV area 390 is seen by both of the cameras, first side camera 315 and front 310, a user may see the one continuous panoramic view formed by the cameras with said object at one size.

Figure 4:
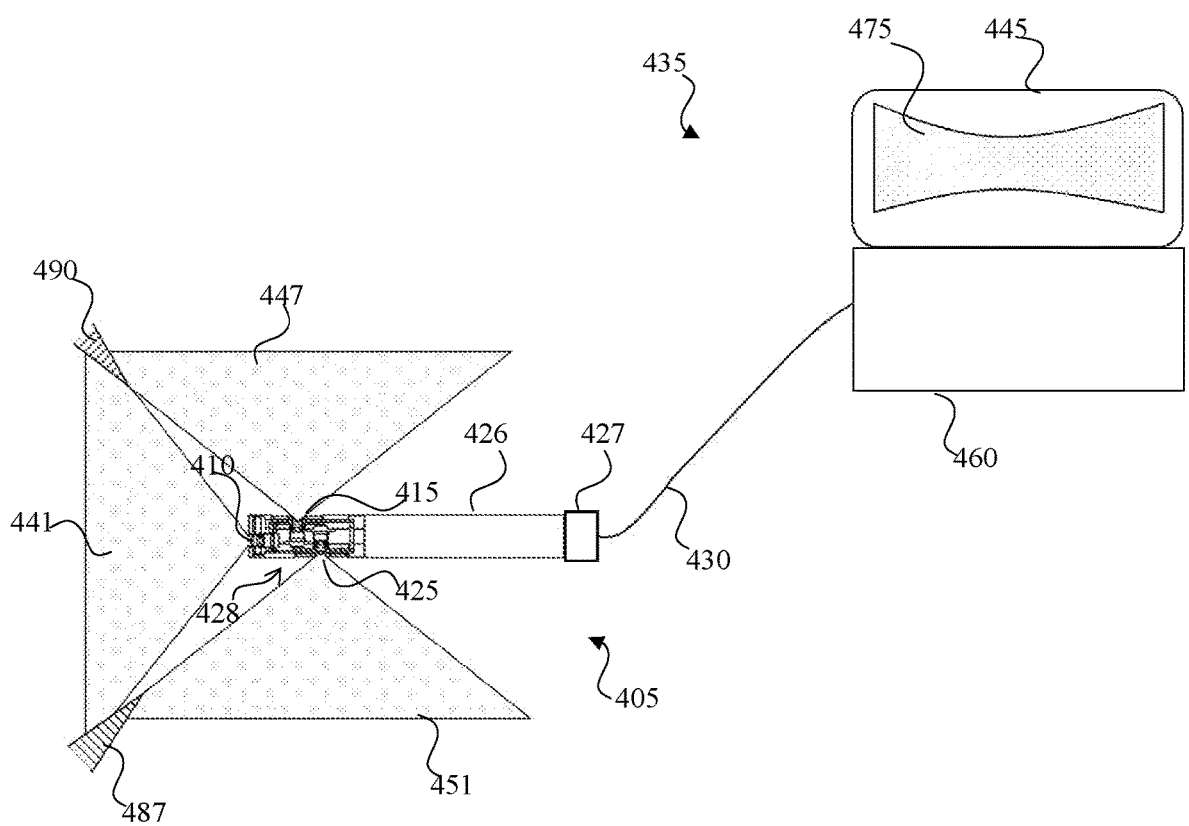
FIG. 4 demonstrates a system designed to create a panoramic and continuous view with areas and objects at the same size, from inputs provided by three cameras situated in a medical imaging device, according to exemplary embodiments of the disclosed subject matter.

FIG. 4 demonstrates a multi imaging rigid scope system designed to create a panoramic and continuous view with areas, points of interest and objects at the same size, from inputs provided by three cameras situated in a multi imaging device, according to exemplary embodiments of the disclosed subject matter. A multi imaging rigid scope system 435 may comprise a multi imaging device 405. Multi imaging device 405 may comprise a handle 427, connected to an elongated rigid shaft 426. The elongated rigid shaft 426 may terminate with a distal tip section 428. The handle 427 may be used for guiding elongated rigid shaft 426 within a body cavity. The handle 427 may comprise one or more buttons and/or switches (not shown) configured to enable a user of the system 425 to control functions such as zoom, focus and elongated movement of rigid shaft 426. The distal tip section 428 of multi imaging device 405 may comprise three cameras, a front camera 410, a second side camera 425 and a first side camera 415. The multi imaging device 405 may further comprise a utility cable 430 connect between handle 427 and a main control unit 460 of multi imaging rigid scope system 435 in order to convey the input received from the cameras of the imaging device 405. Such inputs may be the content from a first side field of view (FOV) 447 captured by first side camera 415, the content from a front field of view (FOV) 441 captured by front side camera 410, and the content from second side field of view (FOV) 451 captured by second side camera 425. In some cases, some of the objects seen by the cameras of the imaging device 405 may be seen in more than one field of view. For example, an object located in a first overlap FOV area 490 may be seen by the first side camera 415 and by the front camera 410, first overlap FOV area 490 refers to areas seen simultaneously at both horizontal FOVs, 441 and 447. Another example may be with an object seen at a second overlap FOV area 487 which can be seen by the second side camera 425 and the front camera 410, second overlap FOV area 487 refers to areas seen simultaneously at both horizontal FOVs, 441 and 451.

In some cases, utility cable 430 may also provide the electrical power required for the operation of the imaging device 405 optical gears. In some other cases, additional and separated connection may be added to convey the electrical power required for the operation of said cameras and illuminators. In another embodiment, wireless communication between handle 427 and main control unit 460 is used.

Main control unit 460 contains the controls required for displaying the images of internal organs captured by the rigid scope cameras. The main control unit 460 may provide or control power transmission to the endoscope's distal tip components, such as for the cameras and illuminators. One or more input devices, such as a keyboard, a mouse, a touch screen and the like may be connected to the main control unit 460 for the purpose of controlling the main control unit 460. The main control unit 460 may also design to receive digital inputs representing content captured by the cameras of the imaging device 405 and convert said digital input to a continuous panoramic view presentation 475 on a display unit 445. Thus, in some cases the main control unit 460 may also comprise a controller designed to perform calculations and execute instructions stored in a computer-readable storage medium. The controller may also comprise a software unit operable on a processor and designed to execute the instructions stored in the computer-readable storage medium. In some embodiments of the present invention, the controller may be located at handle 427. In such embodiments of the specification, the controller may comprise a processor and a computer-readable storage medium for executing the instruction. The controller located at handle 427 may also be configured to communicate with system 460.

In some embodiments of the present invention, the main control unit 460 may be a computerized program operated by a computerized device. Such a computerized device can be a personal computer, a computerized server, a virtual server operated on a dedicated computer, a cluster of servers, a tablet personal computer, and the like. The main control unit 460 may be designed to receive the input from the front camera 410, the second side camera 425 and the first side camera 415, adjust the magnification factor of the cameras in order to create a unified and continuous panoramic view such as continuous panoramic view presentation 475, and display the continuous panoramic view presentation 475 on display unit 445. For example, in case an object is seen at the fields of view of two cameras wherein the distance of the object to one camera is closer than the distance of the object to the other camera, the magnification factor of the other camera may be changed in order to receive said object at approximately similar sizes from both cameras' field of views.

In some cases, main control unit 460 may have a programed method designed to adjust the magnification factor of the cameras, according to the objects seen by two or more cameras. For example, in case an object is seen at first overlap FOV area 490, the main control unit 460 may be able to digitally adjust the magnification factors of the cameras till said object is seen at approximately similar sizes from the field of view of the front camera 410 and the field of view of the first side camera 415, or until the difference of the object size in the two cameras is smaller than a predefined threshold. In some cases, the digitally adjustment of the magnification factors conducted by main control unit 460 may be executed by a method based on digital zoom, wherein the apparent field of view's content of the received video image is decreased or increased in order to receive a larger view or a smaller view respectively, and thereby to receive larger or smaller objects accordingly. In some embodiments of the discloses subject matter, the magnification factor of the cameras the front camera 410, the second side camera 425, and the first side camera 415 may comprise lens assembly and image sensor sizes configured to provide equal magnification factors for object viewed by the cameras. For example, the front camera 410, the second side camera 425, and the first side camera 415 may be configured with essentially equal magnification factors. In such cases, the main control unit 460 may be configured to receive the views captured by the front camera 410, the second side camera 425, and the first side camera 415, digitally adjust the magnification factor of the three cameras and then consolidate the views received from the camera to one continuous and coherent view.

In some cases, only some of the magnification factors of some of the cameras may be digitally adjusted by the main control unit 460. For example, the front camera 410, the second side camera 425, and the first side camera 415 may comprise essentially equal magnification factors. In such cases, the magnification factor of the three cameras may be digitally adjusted by the main control unit 460, and then the be consolidated to one continuous and coherent view.

In some cases, main control unit 460 may have a manual option to manipulate the digital zoom and thereby change the size of the seen objects. For example, a user utilizing the medical imaging device 405 may have a manual option to separately increase and/or decrease the apparent field of views of the front camera 410, the second side camera 425, and the first side camera 415. By changing the apparent field of views of any of the cameras, the objects seen in the FOVs of the cameras can be adjusted till a continuous view, created by the FOVs received from the cameras, is achieved.

In some embodiments of the disclosed subject matter, main control unit 460 may not comprise a display unit such as display unit 445. In such cases, the view received by the main control unit 460 may be sent to an external display unit. In such cases, the main control unit 460 may be configured to create a digital image file of the video imaging. In such cases, the main control unit 460 may also be configured to utilize a communication network and send said digital image file to a remote display unit configured to receive such digital image files. In some cases, the communication network may be internet network, Wi-Fi networks, and the like.

Figure 5:
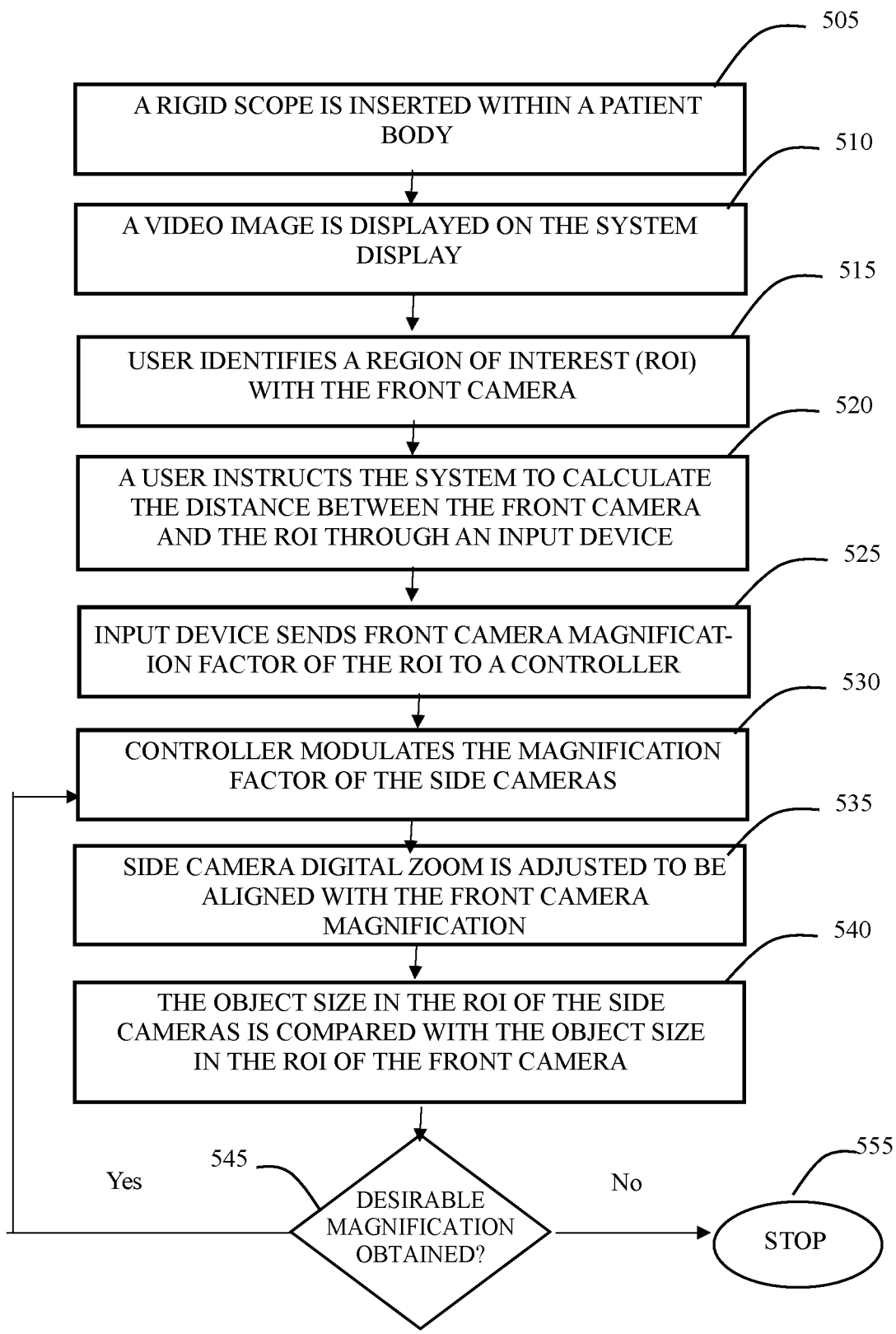
FIG. 5 is a flowchart illustrating a method for obtaining a desirable magnification of a multi camera scope by modifying the digital zoom of side cameras, in accordance with one embodiment of the present invention.

FIG. 5 is a flowchart illustrating a method for obtaining a desirable magnification of a multi camera scope by modifying the digital zoom of side cameras, in accordance with one embodiment of the present invention. At step 505 a user inserts a distal tip section into the patient's body, wherein the distal tip section may be connected to an elongated rigid shaft of a rigid scope. In some cases, the user may operate the elongated rigid shaft having the distal tip at one end with at least two optical gears positioned thereupon and a handle at the other end of the elongated rigid shaft, as aforementioned. The handle of the elongated rigid shaft may be connected to a main control unit and comprise one or more buttons and/or switches configured to enable communicating with the main control unit, as aforementioned. In some cases, the user may also utilize an input device for communicating and controlling the main control unit. For example, the user may utilize a keyboard for the purpose of controlling the main control unit In some cases, the main control unit may also have a controller located at the main control unit or at the handle of the elongated rigid shaft, as aforementioned.

At step 510 video images may be received in a display/monitor of the system. The content of such a video images may be captured by the cameras of the distal tip section. For example, the view captured by the side camera and the front camera may be displayed at the display of the system. In some cases, additional configuration of the display may take place in order to receive a coherent display of the video images transmitted from the elongated rigid shaft, for example resolutions changes, enlarge/stretch the image on the screen, image enhancement and the like. At step 515 the user identifies a region of interest within the lumen with front camera, such that the region of interest is located within the predefined depth of field of the front camera. In some cases, the user utilizing the elongated rigid shaft may be required to adjust the location and/or the direction of the elongated rigid shaft in order to receive an optimal view of the region of interest captured by the front camera.

At step 520 the user instructs the system to calculate the distance between the front camera and the ROI. Thus, the system detects the distal tip position by providing an input through the input device, in order to calculate the distance between the front camera and the ROI. input device such the handle or an external keyboard or touchscreen display. In an embodiment, the handle portion of the rigid scope comprises one or more designated buttons which when toggled or otherwise activated by the user initiate calculating of a distance between front camera and ROI through an input device to be sent to a controller, either an external one or an internal one placed within the handle, as shown in step 525. In one embodiment, the distance between front camera and ROI causes the controller to modulate the magnification factor of the ROI of the front camera according to predefined characters of the front camera, such as sensor size, focal length, F number and more.

For example, a first measured distance between front camera and ROI (caused for example by a button press on the input device) is converged by the system to the magnification factor of the front camera and may cause the controller to increase magnification of each side camera, thereby increasing each side camera digital zoom. In such embodiments, the cameras located within the distal tip component may have the same magnification factors and thereby scale up the view captured by the lens in different sizes. In such case, an object located at a distance to the front camera which is shorter compared to the distance to each side cameras may be captured by at approximately equal magnification factors and thereby allows a creation of a continuous panoramic view formed by the front and side cameras.

At step 530 upon receiving the magnification factor of the front camera by the controller, the controller modulates the magnification factor of the one or more side cameras in accordance with a predefined function that governs the manner in which the allows a creation of a continuous panoramic view formed by the front and side cameras. In one embodiment, the controller applies same function to all the side cameras. In an alternate embodiment, the controller applies a different function to different side cameras.

At step 535 the controller modulates the magnification factor of one or more side cameras operate at one or more modified magnification factors which may be different than their baseline magnification factor, based on the modulation of the magnification factors, for a period of time. In some cases, such a baseline magnification factor may be a predefined value utilized as a default magnification factor. In above embodiment, the modulation is performed in such a manner that the modified magnification factor of one or more cameras allows a creation of a continuous panoramic view formed by the front and side cameras. At step 540, upon receiving the modified magnification factor of one or more side cameras the controller modulates the modified magnification factor of one or more side cameras and the front camera magnification factor such that the system utilizes a continuous panoramic view. In some cases, the controller applies same modified magnification factor to one or more side cameras, in an alternate embodiment, the controller applies a different modified magnification factor to each side camera. In some cases, such a predefined method may be launched automatically by the system. In some other cases, the predefined method for comparing object sizes may be launched manually by the user operating the imaging device.

At step 545 the user operating the system compares the images received from the cameras and verifies whether the desirable magnification factor is obtained and received images form a continuous panoramic view. In some cases, wherein the continuous panoramic view could not be obtained the user may be able to set the system to return to step 530. In other case wherein, the desirable magnification factor is obtained the user may set the system to move to step 555 and halt the magnification factor adjustment process. In some embodiments of the present invention, the user operating the system may be able to conduct the process of obtaining the desirable magnification of a multi camera scope by utilizing one of the side cameras as the reference for other cameras. Thus, in step 530 the user may receive the magnification factor of the first side camera, or in some cases, the second side camera. In such cases, the user may modify the magnification camera of the other cameras, for example the front camera, and/or the side camera for obtaining a continuous panoramic view formed from the images received from the cameras.

Figure 6:
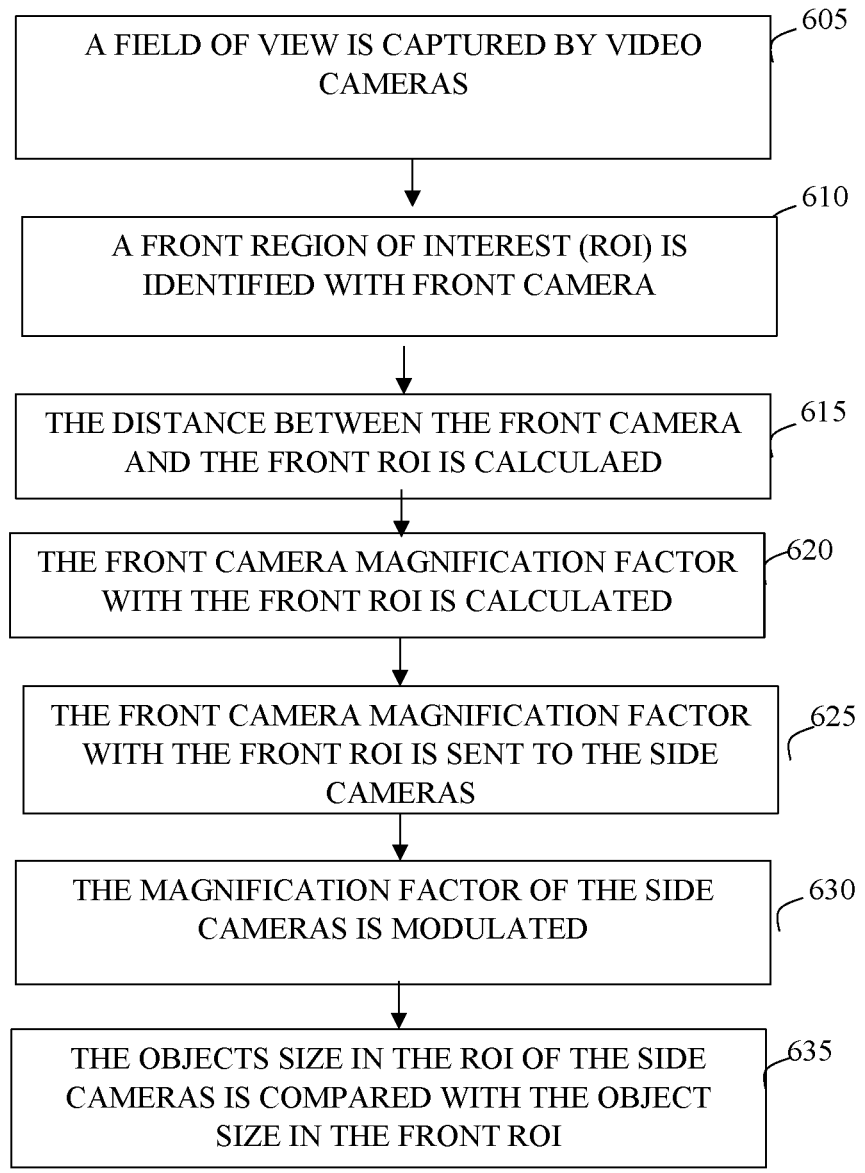
FIG. 6 is a flowchart illustrating a method of coordinating the field views received from at least two cameras and adjusting the magnification factors thereof, in order to receive regions of interest in similar sizes, according to exemplary embodiments of the present invention.

FIG. 6 is a flowchart illustrating a method of coordinating the field views received from at least two cameras and adjusting the magnification factors thereof, in order to receive regions of interest in similar sizes, according to exemplary embodiments of the present invention. At step 605 a field of view is captured by a video camera in a distal tip with at least two optical gears positioned thereupon, wherein the distal tip can be connected to a rigid scope of a medical imaging device. In some cases, the field of view capturing process may be controlled by a user and follow a process of inserting the rigid scope into a patient body, as a part of a medical procedure. At step 610 the front ROI is identified with front camera. In such cases, the front camera may be located at the front planar of the distal tip, as illustrated in FIGS. 1-2. Thus, in some cases, the front ROI may be identified by maneuvering the rigid scope with the patient's body till the user receives the desirable aspect of the front camera's field of view. In some other cases, the user may interact with a system utilized to define the visible objects within the front RO.

At step 615 the distance between the front camera and the front ROI is calculated. In some cases, the user may utilize a computerized mechanism such as a system connected to the rigid scope, for calculating said distance. In some cases, the numeric value of the calculated distance may be stored in a computer-readable storage medium which may be located at the system and connected to the rigid scope. In some other cases, such a computer-readable storage medium may be located at any other computerized device designed to communicate with the rigid scope and receive data therefrom. Communication may be a wire communication and/or wireless communication. At step 620 the value of the calculated distance may be utilized to calculate the front camera magnification factor, according to the front ROI previously obtained. In some cases, the magnification factor calculation process may utilize a baseline magnification factor defined by the image sensor size of the front camera and the focal length of the lens assembly of the front camera. In such cases, the measured distance and the baseline magnification factor may be utilized to produce the front camera magnification factor, according to the current front RO.

At step 625 the front camera magnification factor, according to the current front ROI may be sent to at least one side camera. Thus, in some cases, the front camera magnification factor may be stored in a controller located at the handle of the rigid scope, and thereby can be sent to the at least one side camera. In some other cases, the front camera magnification factor may be stored in a media located at the computerized device connected to the rigid scope, such that the numeric value can then be utilized by the cameras. For example, a system connected to the rigid scope may store the numeric value of the front camera magnification factor in a controller such that the stored value of the front camera magnification factor can be utilized by the controller to calculate additional magnification factors. At step 630 the magnification factor of the at least one side camera may be adjusted for being aligned with the front camera magnification factor. In some cases, the magnification factor adjustment may be via utilizing a digital zoom, wherein the apparent field of view of the received video image is decreased or increased in order to receive a larger view or a smaller view respectively, and thereby to receive larger or smaller objects accordingly.

At step 635 the objects size in the ROI of the at least one side camera is compared with the object size in the front ROI of the front camera. In some cases, the magnification factor of the at least one side camera may be adjusted further in order to receive a desirable object size. The magnification factor adjustment may be required to achieve a continuous panoramic view formed by the front camera and at least one side camera. In some cases, the magnification factor adjustment may be conducted by the system connected to the rigid scope.

While the disclosure has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the disclosed subject matter not be limited to the particular embodiment disclosed as the best mode contemplated for carrying out this invention, but only by the claims that follow.

The invention claimed is:

1. A medical imaging device, comprising:
a rigid elongated member;
a distal tip directly connected to the rigid elongated member, said distal tip comprises a front camera, wherein the front camera comprises a lens assembly and an image sensor providing a focal length and a front camera magnification factor, wherein the front camera is located on a front planar surface of the distal tip and provided a horizontal field of view and;
a first side camera, wherein the first side camera comprises a lens assembly and an image sensor providing a focal length and a first side magnification factor, wherein the first side camera is located on a lateral surface of the distal tip and positioned 5 to 10 millimeters from the front planar surface of the distal tip and provides a horizontal field of view;
wherein differences between the front camera focal length and the first side camera focal length resulting with dissimilar magnification factors between the front camera and the first side camera, wherein an object seen at an overlap area between the horizontal field of view of the front camera and the horizontal field of view of the first side camera is displayed at similar sizes in a display of a continuous panoramic view;
wherein the object is closer to the front camera than to the first side camera, and
a controller designed to receive the object simultaneously captured by the first side camera and the front camera and display the continuous panoramic view formed by the field of view captured by the front camera and the field of view captured by the first side camera for the object which is located at a distance larger than 11 millimeters from said front and first side cameras.

2. The medical imaging device of claim 1, further comprises a second side camera, wherein the second side camera comprises a lens assembly and an image sensor providing a focal length of 3.4 millimeters and a second side camera magnification factor, wherein the second side camera is located on the lateral surface of the distal tip in opposite side to said first side camera and provides a horizontal field of view, and wherein the first side camera is positioned closer to the front planar surface of the distal tip than the second side camera;
wherein differences between the front camera focal length and the second side camera focal length resulting with dissimilar magnification factors between the front camera and the second side camera, wherein an object seen at an overlap area between the horizontal field of view of the front camera and the horizontal field of view of the second side camera is displayed at similar sizes in the display of the continuous panoramic view, wherein the object is closer to the front camera than to the second side camera.

3. The medical imaging device of claim 2, wherein the second side camera magnification factor and the front camera magnification factor are configured to simultaneously capture objects to further be displayed on the image monitor at similar sizes.

4. The medical imaging device of claim 1, wherein the first side camera magnification factor has a larger value than the magnification factor of the front camera for the object located at a distance of 15 to 150 millimeters from said front and first side camera.

5. The medical imaging device of claim 4, wherein the first side camera magnification factor is twice larger than the magnification factor of the front camera for the object located at a distance of 15 to 150 millimeters from said front and first side camera.

6. The medical imaging device of claim 2, wherein the second side camera magnification factor has a larger value than the magnification factor of the front camera for the object located at a distance of 15 to 150 millimeters from said front and second side camera.

7. The medical imaging device of claim 2, wherein the second side camera magnification factor is twice larger than the magnification factor of the front camera for the object located at a distance of 15 to 150 millimeters from said front and second side camera.

8. The medical imaging device of claim 2, wherein the second side camera horizontal field of view is between 80-120 degrees.

9. The medical imaging device of claim 1, wherein the first side camera has a horizontal field of view of between 80-120 degrees.

10. The medical imaging device of claim 1, wherein the front camera horizontal field of view is between 80-120 degrees.

11. The medical imaging device of claim 1, wherein the medical imaging device is connected to a system configured to display the view captured by the first side camera and the front side camera, in a unified and continuous panoramic view.

12. The medical imaging device of claim 11, wherein the controller is further configured to utilize a digital zoom for adjusting the magnification factors of the front camera and the first camera.

13. An imaging method performed in a medical imaging device, comprising:
    capturing a field of view of a front camera having a front camera magnification factor, wherein the front camera is a video camera located at the front plane of the medical imaging device;
    capturing a field of view of a first side camera having a first side magnification factor, wherein the first side camera is located on a lateral surface of the medical imaging device;
    wherein differences between the front camera focal length and the first side camera focal length resulting with dissimilar magnification factors between the front camera and the first side camera;
    generating a continuous panoramic view from a stream of images captured by the front camera and a stream of images captured by the first side camera, the continuous panoramic view comprises an overlap area captured by both the front camera and the first side camera;
    wherein an object seen at the overlap area between the horizontal field of view of the front camera and the horizontal field of view of the first side camera is displayed at similar sizes in a display of a continuous panoramic view;
    wherein the object is closer to the front camera than to the first side camera.

14. The method of claim 13, wherein the first side camera is characterized with a magnification factor configured to increase and/or decrease thereof and thereby to allow viewing objects simultaneously captured by a second side camera and the front camera at similar sizes.

15. The method of claim 13, further comprises capturing a field of view of a second side camera, wherein the second side camera is located at the lateral surface of said medical device in opposite side to said first side camera, wherein the second side camera is characterized with magnification factor configured to increase and/or decrease thereof and thereby to allow viewing object simultaneously captured by the second side camera and the front camera at similar sizes.

16. The method of claim 13, wherein the front camera is provided with a focal length which is different from the focal length of the first side camera.

17. The method of claim 13, further comprises a process for determining the magnification factor by the focal lengths of the front camera and of the first side camera, wherein enlarging the focal length of the front camera and/or the first side camera results in increasing of the magnification factors of the front camera and/or the first side camera, accordingly.

18. The method of claim 13, further comprises a process for determining magnification factor by the digital zoom factor of the front camera and the first side camera, wherein enlarging of the digital zoom factor of the front camera and/or the first side camera results in increasing of the magnification factors of the front camera and/or the first side camera, accordingly.

19. The method of claim 13, further comprises displaying the view captured by the first side camera and/or the front side camera in a unified and continuous panoramic view by a system connected to the medical imaging device.

* * * * *